(12) United States Patent  (10) Patent No.: US 8,439,894 B1
Miller  (45) Date of Patent: May 14, 2013

(54) NEGATIVE PRESSURE BANDAGE WITH INTERNAL STORAGE CHAMBER

(76) Inventor: Larry W. Miller, Lancaster, PA (US)

( * ) Notice: Subject to any disclaimer, the term of this patent is extended or adjusted under 35 U.S.C. 154(b) by 86 days.

(21) Appl. No.: 13/041,710

(22) Filed: Mar. 7, 2011

(51) Int. Cl.
 *A61M 1/00* (2006.01)
 *A61M 27/00* (2006.01)
(52) U.S. Cl.
 USPC .................... 604/543; 604/313; 604/319
(58) Field of Classification Search ......... 604/304–316, 604/319–321, 543; 602/41–58
 See application file for complete search history.

(56) References Cited

U.S. PATENT DOCUMENTS

| 5,636,643 | A | 6/1997 | Argenta | 128/897 |
| 7,361,184 | B2 | 4/2008 | Joshi | 606/213 |
| 7,615,036 | B2 * | 11/2009 | Joshi et al. | 604/313 |
| 2009/0264807 | A1 | 10/2009 | Haggstrom | 602/53 |
| 2009/0299251 | A1 | 12/2009 | Buan | 602/43 |
| 2010/0185163 | A1 * | 7/2010 | Heagle | 604/290 |

FOREIGN PATENT DOCUMENTS

WO  WO 2009/066105  * 5/2009

* cited by examiner

*Primary Examiner* — Kristen Matter
*Assistant Examiner* — Jennifer Deichl
(74) *Attorney, Agent, or Firm* — Miller Law Group, PLLC (57) ABSTRACT

A negative pressure bandage is formed in a two chamber configuration having a lower chamber from which fluids and exudates are collected from an open wound on the patient and an upper chamber that is used to store the collected fluids and exudates removed by an application of a vacuum to the lower chamber. An impermeable layer separates the upper and lower chambers to keep the wound dry and promote healing. A vacuum port interconnects a fluid collection member located in the lower chamber with the upper chamber to allow the application of a vacuum that collects and removes fluids and exudates from the lower chamber. The vacuum pump can be remote and attached to the bandage by tubing or be incorporated into the bandage to provide a self-contained negative pressure bandage. An absorptive pad can be located in the upper chamber to collect and gel the collected fluids.

6 Claims, 7 Drawing Sheets

Fig. 13

NEGATIVE PRESSURE BANDAGE WITH INTERNAL STORAGE CHAMBER

FIELD OF THE INVENTION

The present invention relates generally to negative pressure bandages operable to remove exudates and fluids from a wound and, more particularly, to a bandage structure that has a lower chamber for collecting the exudates and fluid for removal to a secondary bladder above the collection chamber, but within the structure of the bandage.

BACKGROUND OF THE INVENTION

Negative pressure therapy has been utilized for the treatment of a variety of wounds by medical practitioners. Conventional negative pressure bandages are generally large in size and often require the use of complicated equipment such as suction pumps, vacuum pumps and complex electronic controllers to apply a negative pressure within the bandage to draw exudates and fluids away from the wound to a remote collection container. Typically, negative pressure therapy involves other associated equipment, such as the exudates/fluid collection canisters, liquid transporting conduits, and pressure regulators/transducers/sensors. As a result, negative pressure bandages and related equipment tends to be bulky and relatively costly. Such complexity typically requires professional placement of the bandage and connection to the pump and collection canister, followed by consistent, regular patient supervision and monitoring. Generally, negative pressure bandages are applied for approximately two days, at which time the bandage must be removed and replaced by professional technicians.

The rising costs of healthcare and of medical devices, such as negative pressure bandages, provide incentive to develop less expensive equipment, and procedures that are more easily utilized to reduce the costs associated with the use of sue therapy while improving on the effectiveness of the therapy. Simplification of the procedures and the equipment can allow in-home use of such therapies with a minimum of professional supervision and monitoring of the patients. Furthermore, patients continue to demand devices that are more easily portable to allow travel and mobility while utilizing the therapy.

In U.S. Pat. No. 7,615,036, granted to Ashok Joshi, et al on Nov. 10, 2009, a negative pressure bandage is disclosed in which the bandage has a housing that is sealed to the body surface of the patient and defines a liquid retention chamber coupled to a vacuum source to apply a negative pressure on the liquid retention chamber so that the exudates and fluids are drawn into an absorptive material within the liquid retention chamber. This liquid retention chamber is located adjacent to the wound from which the exudates and fluids are removed.

Improvements to negative pressure wound therapy devices can be found in U.S. Patent Publication No. 2009/0299251 of John Buan published on Dec. 3, 2009, to enhance the sealing of the bandage to the body surface of the patient. In this negative pressure wound therapy device, a vacuum is applied to a collection chamber in which an absorptive pad is disposed to collect the exudates and fluids drawn away from the wound by the vacuum (negative pressure). To enhance the connection of the tubing extending between the vacuum pump and the negative pressure therapy device, an extended length connector is disclosed, which will accommodate connection when ACE wrap or other coverings are applied to the exterior of the bandage.

In U.S. Pat. No. 7,361,184, granted on Apr. 22, 2008, to Ashok Joshi, an attempt to provide a self-contained negative pressure wound therapy device is provided so that the device does not require connection to a remote vacuum source. In this negative pressure wound dressing, an absorptive pad is also disposed in the fluid collection chamber, which is located adjacent the wound, the negative pressure drawing the exudates and fluids away from the wound into the absorptive pad. Several early embodiments of negative pressure bandages can be found in U.S. Pat. No. 5,636,643, granted to Louis Argenta, et al on Jun. 10, 1997, all of which, however, utilize a single chamber configuration in which a vacuum is applied to the fluid collection chamber and the exudates and fluid is drawn away through tubing to a remote pump and fluid retention chamber.

A micropump system provides the vacuum source for the negative pressure bandage disclosed in U.S. Patent Publication No. 2009/0264807 filed by Kurt Haggstrom and published on Oct. 22, 2009. This negative pressure dressing is also a single chamber configuration with an absorptive pad placed in contact with the wound while the micropump draws the exudates and fluids from the wound site into the absorptive pad. The micropump can be reusable or disposable. The outer housing layer of the bandage is provided with an opening that enables the absorptive pad to be removed and replaced on a periodic basis.

It would be desirable to provide a self-contained negative pressure bandage to centralize the collection and retention of exudates and fluid from a wound in a manner that removes the exudates and fluids away from the wound site without requiring transportation thereof to a remote retention chamber.

SUMMARY OF THE INVENTION

It is an object of this invention to overcome the disadvantages of the prior art by providing a two chamber negative pressure bandage in which the collected exudates are stored in the upper chamber.

It is another object of this invention to separate the first chamber in which exudates are removed from the wound by an application of a vacuum from a second chamber in which the exudates are stored by an impervious layer.

It is a feature of this invention that the wound is kept dry by the removal of the exudates and fluids to the second chamber.

It is an advantage of this invention that healing of the wound is promoted.

It is another advantage of this invention that the disposal of the collected exudates is accomplished with the disposal of the bandage.

It is another feature of this invention that the vacuum pump can be incorporated into the negative pressure bandage and disposed with the bandage and the collected exudates.

It is still another feature of this invention that a fluid collection member is disposed within the lower chamber between the wound contact member and the impermeable layer to collect fluids and exudates from the wound.

It is yet another feature of this invention that the upper chamber can be provided with vertical structure to prevent the upper chamber from collapsing onto the vacuum port due to the application of the vacuum through the upper chamber.

It is still another feature of this invention that the upper chamber can be provided with an adsorptive pad to collect and gel the fluids and exudates removed from the lower chamber.

It is still a further object of this invention to provide a negative pressure bandage utilizing a two chamber configuration, which is durable in construction, inexpensive of manufacture, carefree of maintenance, facile in assemblage, and simple and effective in use.

These and other objects, features and advantages are accomplished according to the instant invention by providing a negative pressure bandage formed in a two chamber configuration having a lower chamber from which fluids and exudates are collected from an open wound on the patient and an upper chamber that is used to store the collected fluids and exudates removed by an application of a vacuum to the lower chamber. An impermeable layer separates the upper and lower chambers to keep the wound dry and promote healing. A vacuum port interconnects a fluid collection member located in the lower chamber with the upper chamber to allow the application of a vacuum that collects and removes fluids and exudates from the lower chamber. The vacuum pump can be remote and attached to the bandage by tubing or be incorporated into the bandage to provide a self-contained negative pressure bandage. An absorptive pad can be located in the upper chamber to collect and gel the collected fluids.

BRIEF DESCRIPTION OF THE DRAWINGS

The foregoing and other objects, features, and advantages of the invention will appear more fully hereinafter from a consideration of the detailed description that follows, in conjunction with the accompanying sheets of drawings. It is to be expressly understood, however, that the drawings are for illustrative purposes and are not to be construed as defining the limits of the invention.

DETAILED DESCRIPTION OF THE PREFERRED EMBODIMENT

Figure 1:
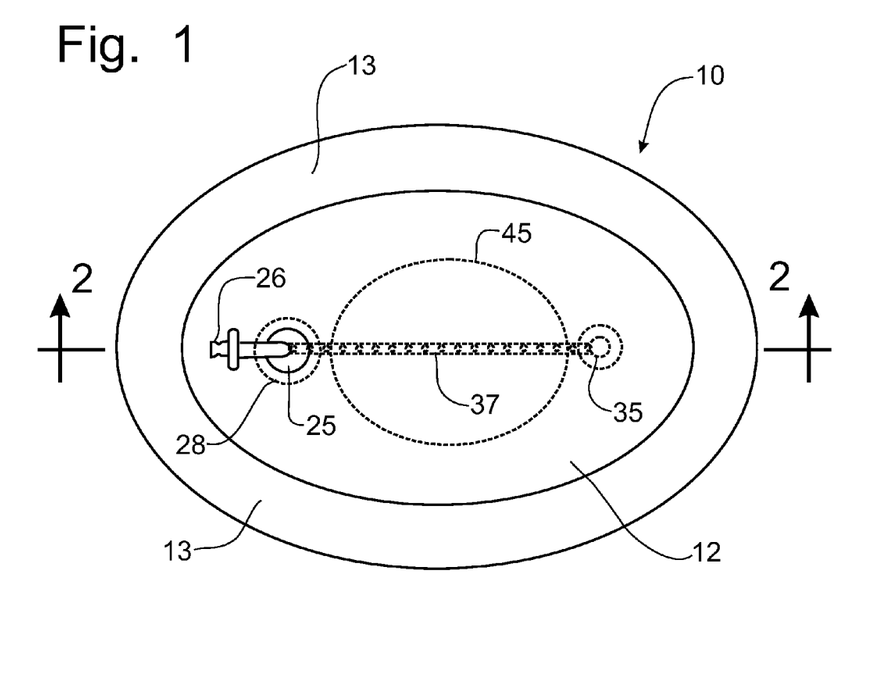
FIG. 1 is a top plan view of a negative pressure bandage incorporating the principles of the instant invention, the absorptive pack in the fluid retention chamber and the fluid collection apparatus in the fluid collection chamber being shown in phantom.
Figure 3:
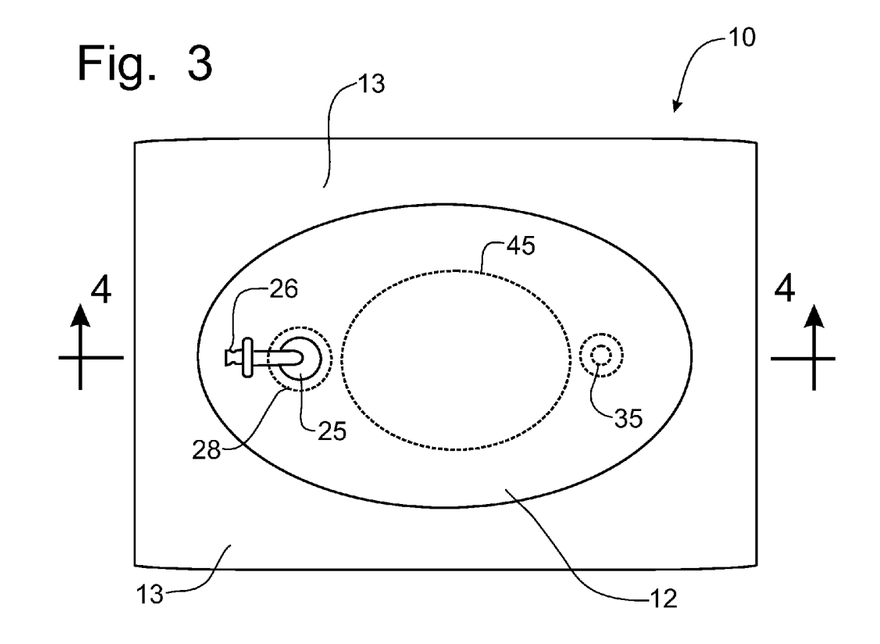
FIG. 3 is a top plan view of a second embodiment of a negative pressure bandage incorporating the principles of the instant invention, the absorptive pack in the fluid retention chamber being shown in phantom.

Referring to the drawings, a negative pressure bandage incorporating the principles of the instant invention can best be seen. The negative pressure bandage 10 has an outer housing 12 that is exposed outwardly from the patient when the bandage 10 is applied to an open wound to remove the exudates and fluids therefrom when connected to a conventional vacuum source (not shown). The outer housing 12 can be formed in any suitable shape, including an oval shape as shown in FIG. 1 or a rectangular shape as depicted in FIG. 3. The vacuum source (not shown) is typically a small pump that is worn by the patient remotely from the bandage 10 to apply a vacuum to the bandage 10 and affect the removal of exudates and fluids from the wound site through conventional tubing (not shown) that is connected to the bandage 10, as will be described in greater detail below.

The bandage 10 has a wound contact panel 15 below the outer housing 12. The wound contact panel 15 can be a layer of gauze, but is preferably a material that will reduce adhesion of the wound contact panel 15 to the underlying wound tissue, such as a silver coated mesh. Surrounding the wound contact panel 15 is a sealing portion 13 of the housing 12 on the underlying surface of the housing 12 which is formed with a suitable adhesive (not shown) and a removable backing member 14 so that the removal of the backing 14 exposes the sealing portion 13 for contact with the body portion of the patient surrounding the wound.

An intermediate fluid impermeable housing member 20 lies between the outer housing 12 and the wound contact panel 13 to separate the outer housing member 12 from the wound contact panel 15 and define separate chambers 30, 40 above and below the intermediate housing member 20. The liquid collection chamber 30 below the intermediate housing panel 20 functions to collect exudates and fluids from the wound being treated, while the liquid retention chamber 40 above the intermediate housing member 20 functions to retain the exudates and fluids collected from the wound.

The outer housing member 12 has a vacuum port 25 formed at one end thereof. The vacuum port 25 can be on any appropriate shape or size, but has connected thereto an adaptor 26 for the attachment of tubing to connect the bandage 10 to a remote, external pump (not shown) to apply a vacuum, or negative pressure, of approximately 75 to 125 mmHg to the liquid retention chamber. Internally of the vacuum port 25, a hydrophobic, or fluid impermeable, filter 28 is attached to the vacuum port 25 to prevent fluids from passing through the vacuum port 25 while negative pressure is applied to the adaptor 26. One material that can prevent the passage of fluid through the vacuum port 25 while allowing a vacuum to be applied to the fluid retention chamber is GORE-TEX® material.

Preferably, a gelling agent, such as sodium carboxy methyl cellulose, and medicaments, such as an antimicrobial agent, will be added into the liquid retention chamber 40 to convert liquids into a gel-like substance and to prevent the growth of bacterial therein. Optionally, the liquid retention chamber 40 could house an absorptive pad 45, which can contain the gelling agent and medicaments, and provide a structure for the retention of the exudates and fluids within the liquid retention chamber 40. The absorptive pad 45 would be capable of absorbing exudates and fluids transferred from the wound, as will be described in greater detail below, while continuing to allow a vacuum to be applied to the liquid retention chamber 40 to draw the exudates and fluids from the wound site. The absorptive pad 45 may be a sponge, gauze, or super-absorbent materials including super-absorbent or combinations thereof.

The intermediate housing member 20 is formed with a connective port 35 at one end of the intermediate housing member 20, preferably in opposition to the vacuum port 25 so that one port is at one end of the bandage 10 while the other port is at the opposite end, to allow flow communication between the liquid retention chamber 40 and the liquid collection chamber 30. The connective port 35 is connected to a fluid collection member 37 that the vacuum applied to the fluid retention chamber 40 through the vacuum port 25 is communicated to the fluid collection chamber 30 through the fluid collection member 37.

Figure 2:
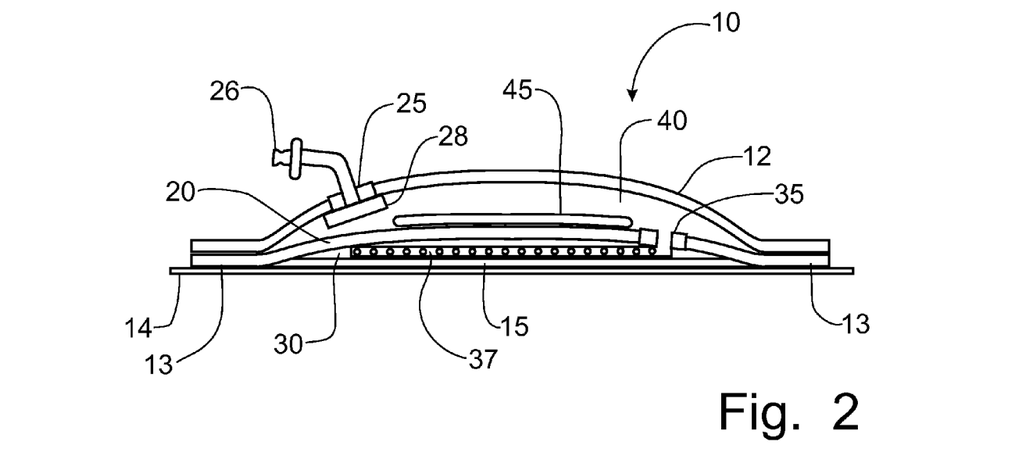
FIG. 2 is a cross-sectional view of the negative pressure bandage corresponding to lines 2-2 of FIG. 1 to show the configuration thereof with the lower fluid collection chamber and the upper fluid retention chamber.
Figure 4:
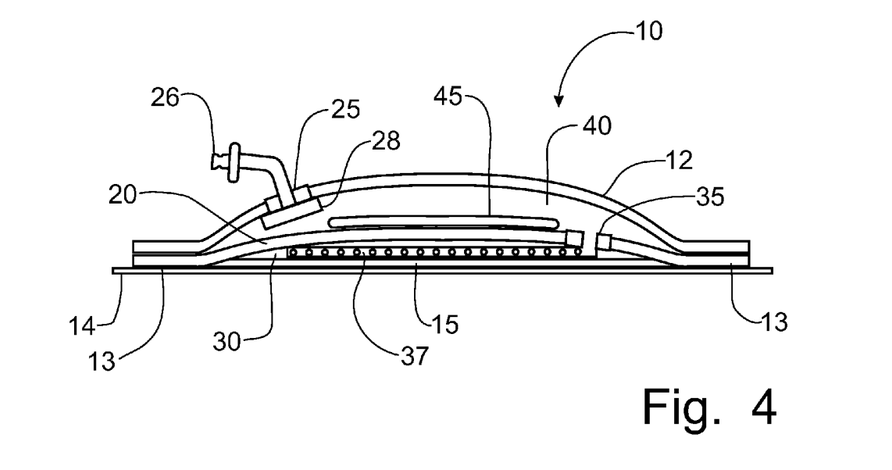
FIG. 4 is a cross-sectional view of the negative pressure bandage corresponding to lines 4-4 of FIG. 2 to show the configuration thereof with the lower fluid collection chamber and the upper fluid retention chamber.
Figure 5:
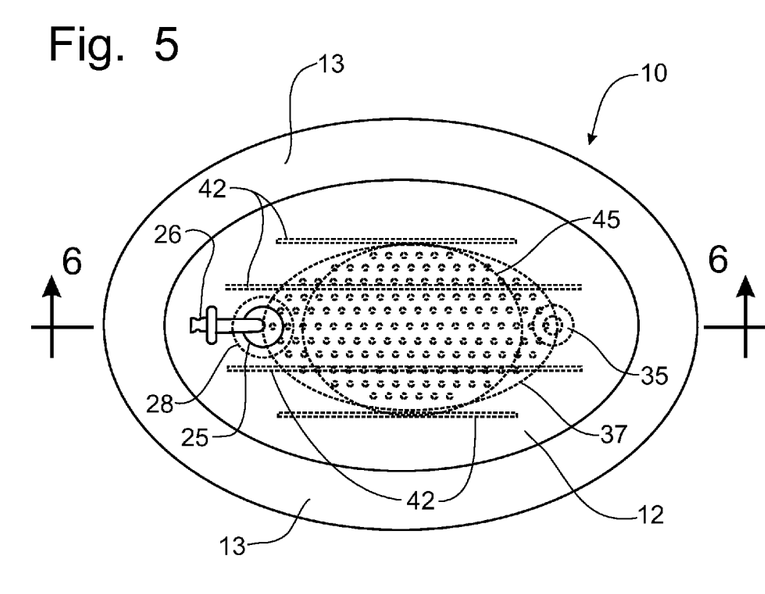
FIG. 5 is a top plan view of a third embodiment of a negative pressure bandage incorporating the principles of the instant invention, the fluid collection apparatus in the fluid collection chamber and the structural supports for the fluid retention chamber being shown in phantom.
Figure 6:
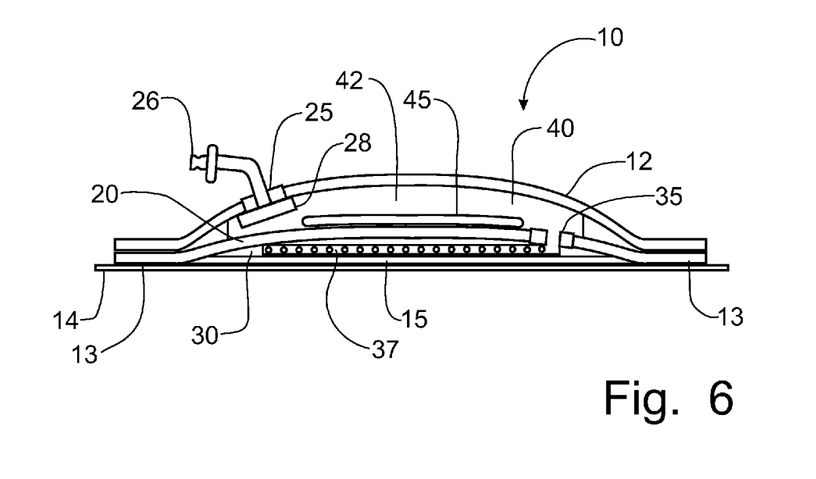
FIG. 6 is a cross-sectional view of the negative pressure bandage corresponding to lines 6-6 of FIG. 5 to show the configuration thereof with the lower fluid collection chamber and the upper fluid retention chamber having structural supports.

The fluid collection member 37 is preferably a hollow device having a plurality of openings therein to allow exudates and fluids to enter into the interior of the fluid collection member 37 as a result of the applied vacuum communicated thereto through the connective port 35. The fluid collection member 37 can be any suitable shape, such as an elongated, linear tube as shown in FIGS. 1, 2 and 4, or an oval member as depicted in FIGS. 5 and 6, depending on the size and shape of the wound to be treated. The fluid collection member 37 is preferably positioned above the wound contact panel 15 so that exudates and fluids will be drawn away from the wound through the wound contact panel 15 and into the fluid collection member 37 to be conveyed through the connective port into the fluid retention chamber 40. In this manner, the exudates and fluids are not retained within the fluid collection chamber 30 in proximity to the wound, allowing the wound to heal quicker.

Since the outer housing member 12 and the intermediate housing member 20 are flexible in nature, the fluid retention chamber 40, as is shown in FIGS. 5 and 6, may require vertical structure, such as pleats 42 or stays, within the liquid retention chamber 40 so that the fluid retention chamber 40 does not collapse onto the vacuum port 25 or the connective port 35 and prevent the application of the negative pressure from the vacuum port 25 to the fluid collection member 37. In such as structure, the gelling agent and/or the absorptive pad 45 would be located between, or perhaps beneath, each of the pleats 42 so that the exudates and fluids drawn from the fluid collection chamber 30 are distributed throughout the fluid retention chamber 40.

Figure 7:
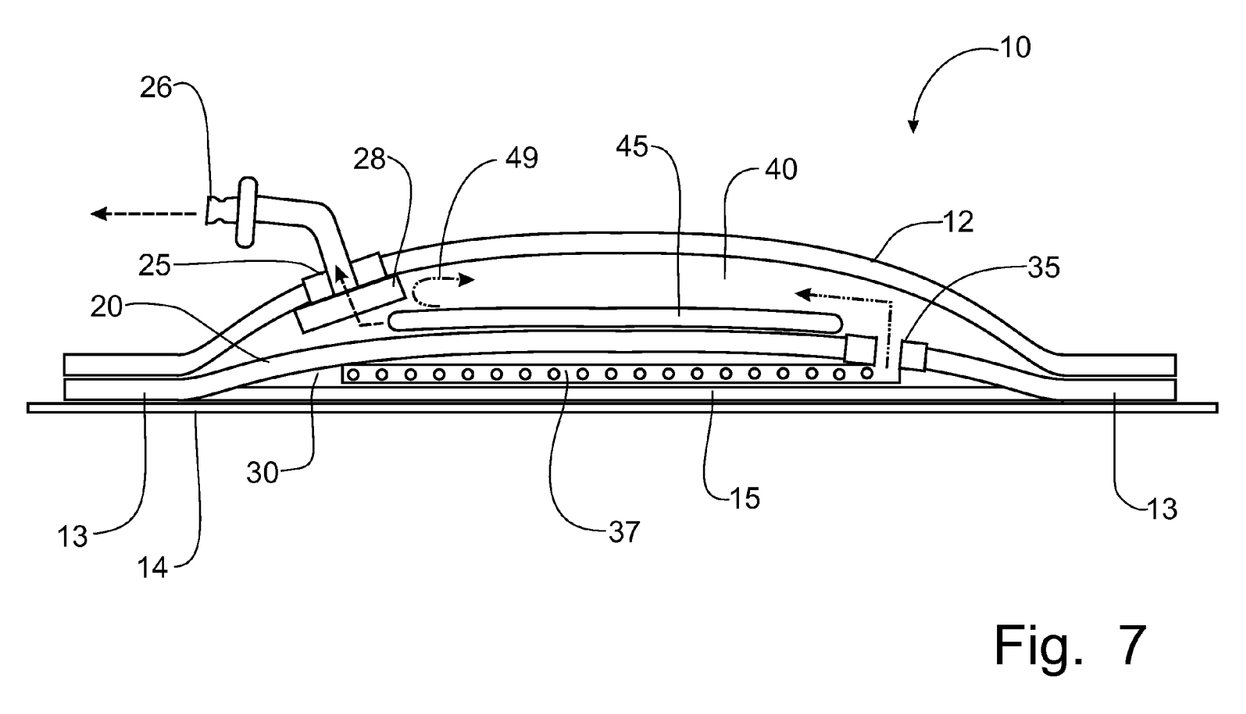
FIG. 7 is an enlarged cross-sectional view of the negative pressure bandage as shown in FIGS. 2 and 4 to depict the operation thereof.

The general operation of the bandage 10 is depicted in FIG. 7. The adaptor 28 is connected through tubing (not shown) to a vacuum source (not shown) to apply a negative pressure through the vacuum port 25 to the fluid retention chamber 40. The vacuum is applied to the fluid collection member 37 in the fluid collection chamber 30 through the open connective port 35 to draw exudates and fluids from the wound site up through the wound contact panel 15 into the interior of the fluid collection member 37. The vacuum, or negative pressure, pulls the exudates and fluids up through the connective port 35 into the fluid retention chamber 40 toward the vacuum port 25. The hydrophobic or fluid impermeable filter 28 rejects the passage of exudates and fluids through the vacuum port, as is represented by line 49. The exudates and fluids interact with the gelling agent and or become absorbed into the absorptive pad 45 to accumulate within the fluid retention chamber.

Preferably, the bandages will come in a variety of sizes and capacities. One particular embodiment would provide for a capacity of approximately 50 cc of exudates and fluids within the fluid retention chamber 40 to provide approximately two days of negative pressure wound therapy for the patient before the bandage would need to be changed. Obviously, certain wound conditions would require larger bandages with greater capacities to accommodate two days of negative pressure wound therapy. Thus, a professional technician would only need to visit, or the patient would only need to change the bandage, every other day.

One skilled in the art will recognize that the application of a negative pressure to the bandage 10 will require a good seal between the sealing portion 13 of the bandage 10 and the skin of the patient around the wound site. To assure an adequate seal around the bandage 10, a stomahesive paste is preferably applied to the sealing portion 13 of the bandage before being affixed to the body portion of the patient. In some instances, a wrapping, such as an ACE wrap, around the bandage 10 is helpful in retaining the bandage in place with a sealed connection with the body portion of the patient.

An alternative arrangement of the bandage 10 is depicted in FIGS. 8-11 in which the pump system 50 supplying the vacuum to the fluid collection member 37 is housed within the fluid retention chamber 40. The pump system 50 includes a miniature pump or micropump 52, such as the micropump manufactured by Piab Vacuum Products in Hingham, Mass., having a length ranging from about 1 to 3 inches and a relatively small diameter, preferably, no greater than about one inch. However, the micropump 52 may be any type of pump that is biocompatible and can maintain adequate and therapeutic vacuum levels in the range of 75 to 125 mmHg. Preferably, the micropump 52 is mounted on the connective port 35 to apply negative pressure directly to the fluid collection member 37 positioned within the fluid collection chamber 30. The micropump 52 is preferably disposable and contains a power source, such as an internal self-contained battery source, that will enable the micropump 52 to be operative for at least 48 hours until the bandage is to be replaced. A pressure sensor or transducer to monitor pressure adjacent the micropump 52, or selected locations displaced from the micropump 52, and a control mechanism may also be needed and could be mounted on the outer housing member 12 where the output therefrom would be visible to the patient.

The output of the micropump 52 may be increased or decreased, or initiated or discontinued, as enabled by the control mechanism. The pressure sensor would also provide information to assist in detecting a leak in the bandage 10 if the optimal negative pressure is not achieved. The control mechanism may also have an alarm such as a visual, audio or tactile sensory alarm to indicate to the user when specific conditions have been met, such as a loss of vacuum.

Figure 8:
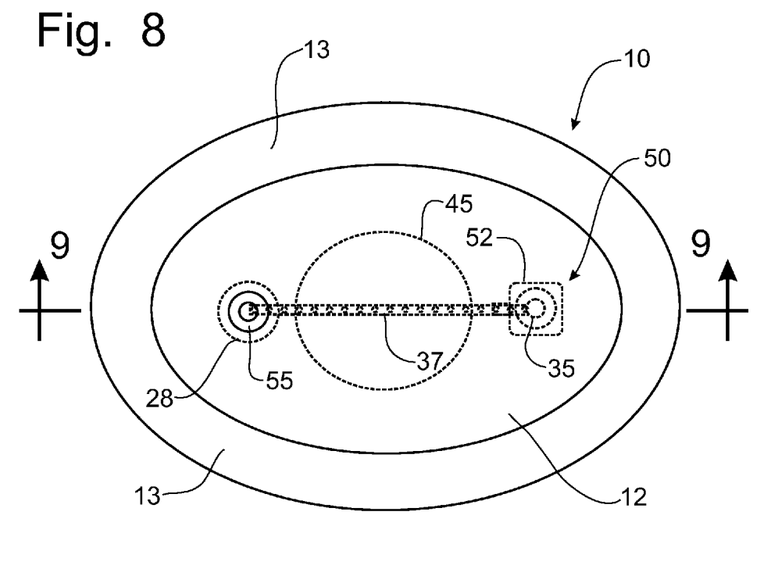
FIG. 8 is a top plan view of a fourth embodiment of a negative pressure bandage utilizing a micropump to provide a vacuum source to draw the exudates and fluids from the fluid collection apparatus into the upper fluid retention chamber, the absorptive pack and the micropump in the fluid retention chamber being shown in phantom.
Figure 9:
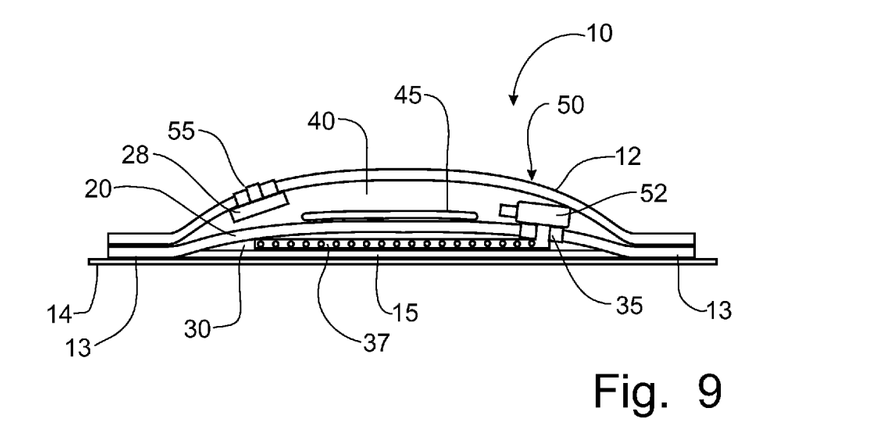
FIG. 9 is a cross-sectional view of the negative pressure bandage corresponding to lines 9-9 of FIG. 8 to show the configuration thereof with the lower fluid collection chamber and the upper fluid retention chamber.

In FIGS. 8 and 9, an outlet vent 55 may be needed to allow the micropump 52 to generate the requisite vacuum for application to the fluid collection member 37. In this embodiment, the hydrophobic or fluid impermeable filter 28 would be associated with the vent port 55 to retain the exudates and fluids within the fluid retention chamber 40. Furthermore, the vent port 55 could incorporate a pressure relief valve that will retain the negative pressure within the fluid collection member 37. Otherwise, the bandage 10 operates as noted above with the exudates and fluids being drawn from the fluid collection chamber 30 via the fluid collection member 37 and the micropump 52 into the fluid retention chamber 40. Once in the fluid retention chamber 40, the exudates and fluids will react with the gelling agent or be absorbed into the absorptive pad 45 so as to be accumulated within the fluid retention chamber 40. The hydrophobic, or fluid impermeable, filter 28 prevents the exudates and fluids from leaving the fluid retention chamber 40 through the vent port 55. Preferably, the bandage 10 will be removed and properly discarded every other day and replaced with a fresh bandage 10 having a new micropump 52 and fresh battery.

Figure 10:
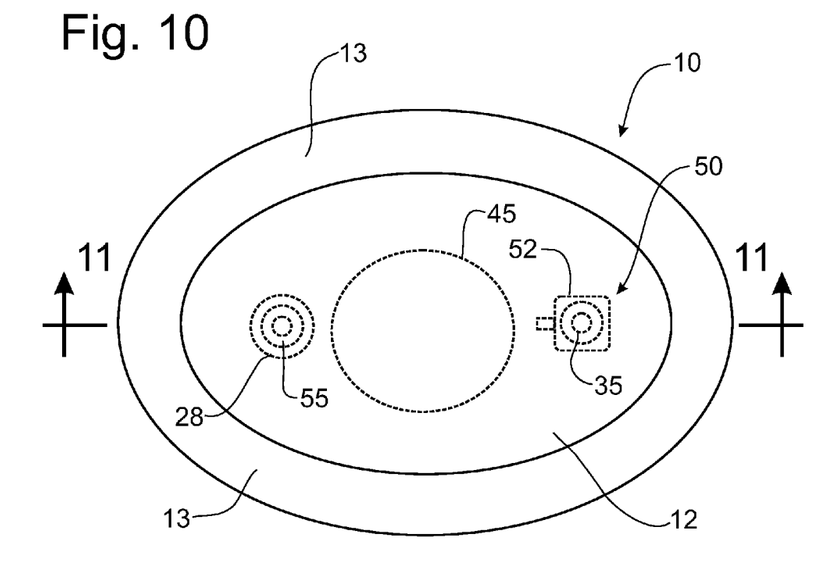
FIG. 10 is a top plan view of a fifth embodiment of a negative pressure bandage similar to that of FIG. 8, but providing a recirculation through the fluid collection apparatus, the absorptive pack in the fluid retention chamber being shown in phantom.
Figure 11:
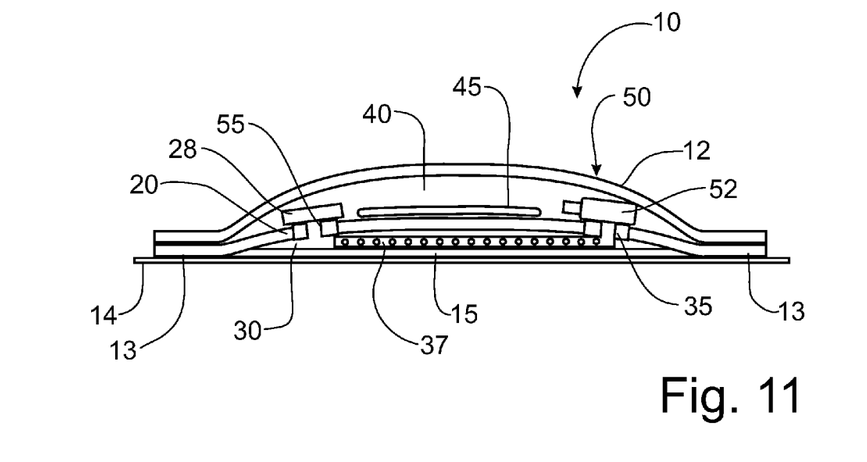
FIG. 11 is a cross-sectional view of the negative pressure bandage corresponding to lines 11-11 of FIG. 10 to show the configuration thereof with the lower fluid collection chamber and the upper fluid retention chamber.

Alternatively, as is depicted in FIGS. 10 and 11, the vent port 55 is placed into the opposing end of the intermediate housing member 20 from the connective port 35 and the associated micropump 52. The hydrophobic, or fluid impermeable, filter 28 would be associated with the vent port 55 to prevent exudates and fluids accumulating in the fluid retention chamber 40 from returning to the fluid collection chamber 30. The micropump 52 would draw a vacuum on the fluid collection member 37 while circulating gases, such as air back into the fluid collection chamber 30 to facilitate the movement of exudates and fluids through the fluid collection member 37 into the fluid retention chamber 40, where the gelling agent and/or the absorptive pad 45 would help to retain the exudates and fluids within the fluid retention chamber 40.

Figure 12:
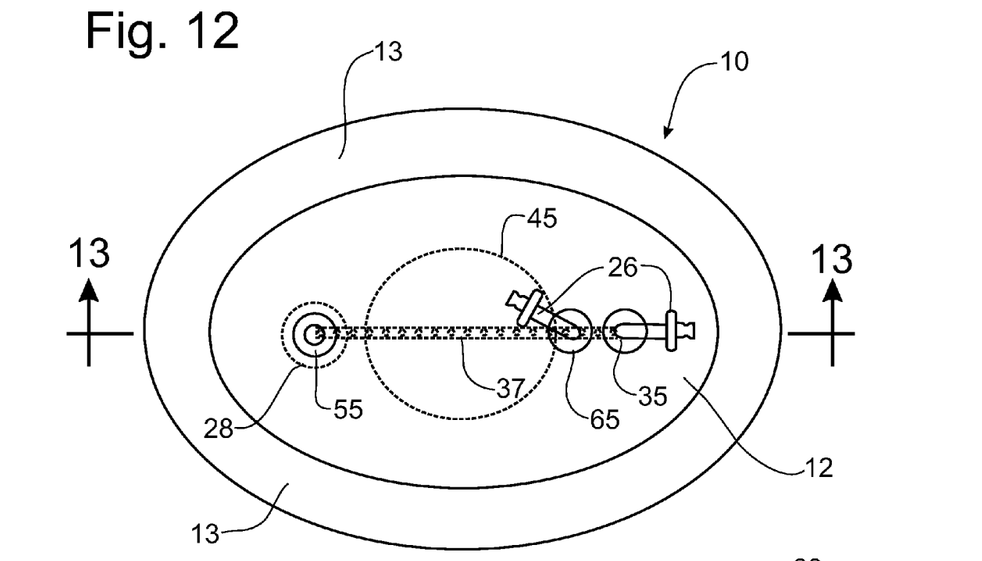
FIG. 12 is a top plan view of a sixth embodiment of a negative pressure bandage providing a removal of the fluids from the wound at the lower chamber through a remote pump and the discharge of the collected fluids from the pump into the upper storage chamber of the bandage.
Figure 13:
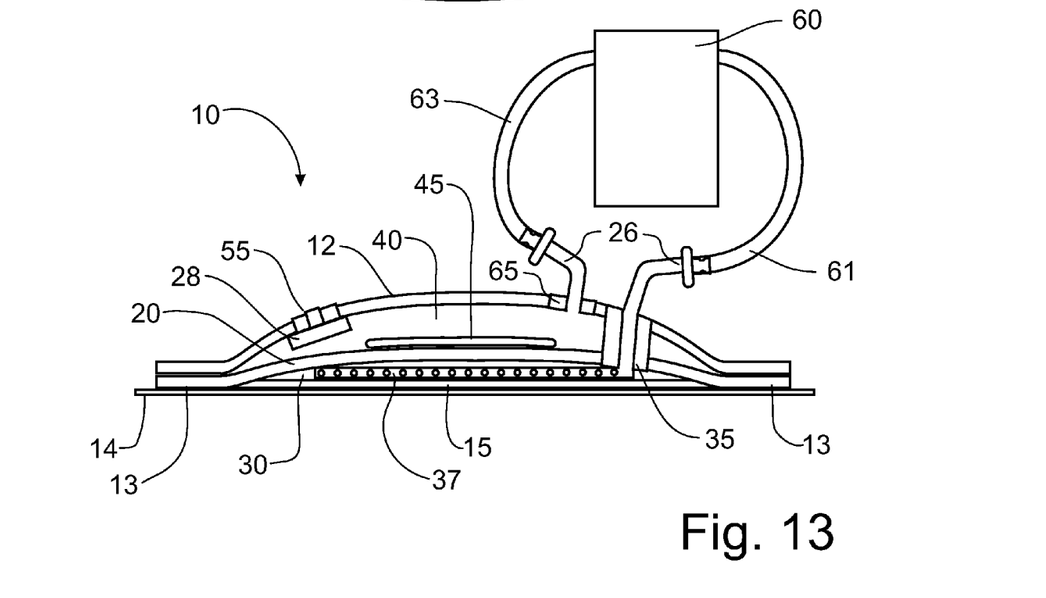
FIG. 13 is a cross-sectional view of the negative pressure bandage corresponding to lines 13-13 of FIG. 12 to show the configuration thereof.

A further alternative arrangement of the bandage 10 is depicted in FIGS. 12 and 13 in which the vacuum pump 60 supplying the vacuum to the fluid collection member 37 is located remotely from the bandage 10, such as being mounted on the patient's belt. The pump 60 is attached via a first tubing member 61 and an adapter 26 to the connective port 35 to apply negative pressure directly to the fluid collection member 37 positioned within the lower fluid collection chamber 30. The pump 60 is typically battery powered to enable the pump 60 to be operative for at least 48 hours until the bandage is to be replaced. The conventional pump 60 is operable to apply a constant vacuum to the fluid collection member and will normally have a display to reflect the operation of the pump 60.

The fluids and exudates collected by the fluid collection member 37 and travel to the pump 60 through the first tubing member 61 and then is discharged from the pump 60 through a second tubing member 63 that is connected to a second connective port 65 via a second adapter 26 to deliver the collected fluids and exudates into the upper storage chamber 40. As described above, the upper storage chamber 40 can be provided with an absorptive pad 45 to absorb and gel the collected fluids. Thus, the fluids and exudates collected from the lower chamber are stored in the upper chamber separated by the impermeable intermediate housing member 20.

As depicted in the embodiment of FIGS. 8 and 9, an outlet vent 55 may be needed to allow the release of air from the upper chamber 40. Preferably, a hydrophobic or fluid impermeable filter 28 would be associated with the vent port 55 to retain the exudates and fluids within the fluid retention chamber 40. Furthermore, the vent port 55 could incorporate a pressure relief valve that will allow a predetermined amount of pressure to be retained within the upper storage chamber 40. The hydrophobic, or fluid impermeable, filter 28 prevents the exudates and fluids from leaving the fluid retention chamber 40 through the vent port 55. Preferably, the bandage 10 will be removed and properly discarded every other day, along with the tubing, with a fresh bandage applied to the wound and fresh tubing interconnecting the pump 60 and the adapters 26 in the proper manner.

The invention of this application has been described above both generically and with regard to specific embodiments. Although the invention has been set forth in what is believed to be the preferred embodiments, a wide variety of alternatives known to those of skill in the art can be selected within the generic disclosure. It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

What is claimed is:

1. A negative pressure bandage connectable to a vacuum pump to create a vacuum for the collection of fluids from an open wound, comprising:
    an outer housing having an adhesive sealing portion extending around the perimeter of said housing;
    a lower fluid collection chamber surrounded by said sealing portion and having a wound contact member;
    an upper fluid storage chamber separated from said lower fluid collection chamber by a panel formed of gas and liquid impermeable material, said upper fluid storage chamber including a connection port having a fluid impermeable filter positioned to prevent the passage of fluids from said upper storage chamber through said connection port so that fluids collected from said lower fluid collection chamber are retained in said upper fluid storage chamber; and
    a vacuum port connected in flow communication with said lower fluid collection chamber, said vacuum port being operably connected to said vacuum pump to apply a vacuum to said lower fluid collection chamber for the collect and extract fluids therefrom, said collected fluids being delivered to said upper fluid storage chamber to extract said collected fluids from said lower fluid collection chamber away from said open wound, said vacuum port being connected to said vacuum pump mounted within said outer housing to collect fluids from said lower chamber and discharge the collected fluids into said upper chamber, said panel including a pressure relief port to allow air to move from said upper storage chamber into said lower fluid collection chamber.

2. The negative pressure bandage of claim 1 wherein said connection port forms a passageway from said upper storage chamber for connection to said vacuum pump to apply said vacuum to said upper storage chamber to extract fluids from said lower chamber through said vacuum port into said upper chamber.

3. The negative pressure bandage of claim 1 wherein said upper chamber is formed with vertical structure to prevent said outer housing from collapsing onto said vacuum port when said vacuum pump apples a vacuum thereto.

4. The negative pressure bandage of claim 1 wherein said vacuum port is connected to said vacuum pump mounted within said outer housing to collect fluids from said lower chamber and discharge the collected fluids into said upper chamber, said connection port in said outer housing providing a pressure relief port to vent air from said upper storage chamber.

5. In a negative pressure bandage assembly including a vacuum pump and a negative pressure bandage sealed around an open would and connected to said vacuum pump to permit the extraction of fluids from said open wound through an application of vacuum to said negative pressure bandage, the improvement comprising:

an outer housing having an adhesive sealing portion extending around the perimeter of said housing and defining a lower fluid collection chamber surrounded by said sealing portion and an upper fluid storage chamber separated from said lower fluid collection chamber by a panel formed of gas and liquid impermeable material, said outer housing including a connection port attached to said vacuum pump to apply the vacuum to said upper fluid storage chamber, said connection port having a fluid impermeable filter to prevent the passage of fluids from said upper fluid storage chamber, said panel including a pressure relief port to allow air to move from said upper storage chamber into said lower fluid collection chamber; and a vacuum port connected in flow communication with said lower fluid collection chamber, said vacuum port being operably connected to said vacuum pump to apply a vacuum to said lower fluid collection chamber for the collect and extract fluids therefrom, said collected fluids being delivered to said upper fluid storage chamber for storage therein to remove said collected fluids from said lower fluid collection chamber away from said open wound.

6. A negative pressure bandage assembly for the collection of fluids from an open wound through use of negative pressure applied to said open wound, comprising:

a negative pressure bandage sealed around said open wound and including:

an outer housing having an adhesive sealing portion extending around the perimeter of said housing and defining a lower fluid collection chamber surrounded by said sealing portion and an upper fluid storage chamber separated from said lower fluid collection chamber by a panel formed of gas and fluid impermeable material, said outer housing including a pressure relief port formed in said panel to vent air from said upper fluid storage chamber into said lower fluid collection chamber, said pressure relief port having a fluid impermeable filter to prevent the passage of fluids from said upper fluid storage chamber;

a vacuum port connected in flow communication with said lower fluid collection chamber, said vacuum port being operable to apply the negative pressure to said lower fluid collection chamber for the collect and extract fluids therefrom, said collected fluids being delivered into said upper fluid storage chamber for storage therein through said vacuum port such that said collected fluids are extracted from said lower fluid collection chamber away from said open wound;

a vacuum pump mounted on said vacuum port to apply negative pressure to said lower fluid collection chamber, said vacuum pump being positioned within said upper storage chamber to extract fluids from said lower chamber and discharge the fluids into said upper chamber.

* * * * *